US011259689B2

(12) United States Patent
Shimoyama

(10) Patent No.: US 11,259,689 B2
(45) Date of Patent: Mar. 1, 2022

(54) ENDOSCOPE SYSTEM, PROCESSOR AND ENDOSCOPE

(71) Applicant: OLYMPUS CORPORATION, Hachioji (JP)

(72) Inventor: Masanori Shimoyama, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 301 days.

(21) Appl. No.: 16/688,652

(22) Filed: Nov. 19, 2019

(65) Prior Publication Data
US 2020/0154986 A1   May 21, 2020

(30) Foreign Application Priority Data
Nov. 21, 2018   (JP) .............................. JP2018-218015

(51) Int. Cl.
*A61B 1/00* (2006.01)
*A61B 5/06* (2006.01)

(52) U.S. Cl.
CPC ...... *A61B 1/00188* (2013.01); *A61B 1/00009* (2013.01); *A61B 1/00158* (2013.01); *A61B 5/065* (2013.01)

(58) Field of Classification Search
CPC ............ A61B 1/00006; A61B 1/00057; A61B 1/00188; A61B 1/00009; A61B 1/00158; A61B 5/065; G02B 23/2438; H04B 3/28; H04B 3/30; H04B 3/32; H04B 3/478; H04B 1/0475
See application file for complete search history.

(56) References Cited

U.S. PATENT DOCUMENTS 5,490,015 A *  2/1996  Umeyama ................. G02B 7/08
                                        359/813
6,059,718 A *  5/2000  Taniguchi ............. A61B 1/0005
                                        600/117
(Continued)

FOREIGN PATENT DOCUMENTS

JP       2015088956 A       5/2015

OTHER PUBLICATIONS

U.S. Appl. No. 16/693,217; First Named Inventor: Rintaro Nishihara; Title: "Endoscope System, Processor, and Endoscope"; filed Nov. 22, 2019.
(Continued)

*Primary Examiner* — Alexandra L Newton
*Assistant Examiner* — Jae Woo
(74) *Attorney, Agent, or Firm* — Holtz, Holtz & Volek PC

(57) ABSTRACT

An endoscope system includes an endoscope and a processor. The endoscope includes: an actuator including a coil configured to cause a movable lens and a magnet to move by application of a drive signal; a position sensor configured to output a position detection signal showing a position of the movable lens according to a magnetic flux of the magnet; and an endoscope memory storing correction information for correcting crosstalk onto the position detection signal by the magnetic flux of the coil. The processor includes a drive controller configured to correct the position detection signal based on the drive signal and the correction information and output the drive signal based on a target position and the corrected position detection signal, to the actuator.

12 Claims, 7 Drawing Sheets

(56) References Cited

U.S. PATENT DOCUMENTS

| | | | | |
|---|---|---|---|---|
| 7,149,419 B2* | 12/2006 | Akada | G02B 27/646 |
| | | | 396/55 |
| 8,817,169 B2* | 8/2014 | Kawada | G02B 7/102 |
| | | | 348/352 |
| 9,563,103 B2* | 2/2017 | Takeuchi | G03B 5/02 |
| 9,606,371 B2* | 3/2017 | Takeuchi | H04N 5/2328 |
| 9,742,257 B2 | 8/2017 | Shimoyama | |
| 9,769,384 B2 | 9/2017 | Nishihara | |
| 10,165,184 B2 | 12/2018 | Nishihara | |
| 10,379,373 B2 | 8/2019 | Nishihara | |
| 2008/0122448 A1* | 5/2008 | Pischl | G01R 27/06 |
| | | | 324/600 |
| 2009/0280757 A1* | 11/2009 | Zhu | H04B 1/0475 |
| | | | 455/114.1 |
| 2015/0057053 A1* | 2/2015 | Zhang | H01Q 21/28 |
| | | | 455/575.5 |
| 2015/0065071 A1* | 3/2015 | Trotta | H03D 7/1458 |
| | | | 455/114.2 |
| 2016/0073027 A1* | 3/2016 | Noguchi | G02B 27/646 |
| | | | 348/208.6 |
| 2016/0212344 A1* | 7/2016 | Takeuchi | G02B 27/646 |
| 2020/0268233 A1* | 8/2020 | Shimoyama | A61B 1/00188 |

OTHER PUBLICATIONS

U.S. Appl. No. 16/780,774, First Named Inventor: Masanori Shimoyama; Title: "Endoscope System, Processor, Calibration Apparatus, and Endoscope"; filed Feb. 3, 2020.

\* cited by examiner

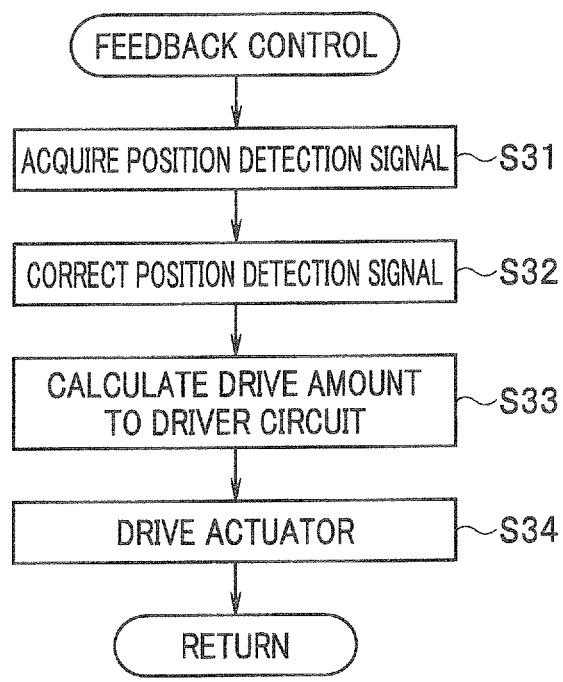

ENDOSCOPE SYSTEM, PROCESSOR AND ENDOSCOPE

CROSS REFERENCE TO RELATED APPLICATION

This application claims benefit of Japanese Application No. 2018-218015 filed in Japan on Nov. 21, 2018, the entire contents of which are incorporated herein by this reference.

BACKGROUND OF THE INVENTION

1. Field of the Invention

The present invention relates to an endoscope system that adjusts an image forming state of an objective optical system by an actuator, a processor and an endoscope.

2. Description of the Related Art

Conventionally, in an image pickup apparatus such as a digital camera, focus adjustment and zoom adjustment have been performed using an actuator.

For example, Japanese Patent Application Laid-Open Publication No. 2015-88956 describes a technique for, at the time of driving a shake correcting member (an image sensor or a lens) by a driving coil in a digital camera, which is an image pickup apparatus, detecting a position of the shake correcting member by a magnetic sensor (a hall sensor). The magnetic sensor, however, not only detects magnetism corresponding to the position of the shake correcting member but also detects magnetism generated by the driving coil as noise. Therefore, a noise coefficient is calculated in advance from a drive signal and a detection signal of the magnetic sensor when the drive signal is outputted to the driving coil to remove a noise signal component corresponding to the magnetism generated by the driving coil, from the detection signal of the magnetic sensor.

At the time of performing measurement for calculation of the noise coefficient, the image sensor (a movable stage) is locked not to move or the measurement is performed before mounting the image sensor (the movable stage) so that the hall sensor is not influenced by change in a magnetic force of a magnet as described in paragraph [0051] and the like of the gazette.

SUMMARY OF THE INVENTION

An endoscope system according to one aspect of the present invention is an endoscope system including an endoscope and a processor to which the endoscope is connected, wherein the endoscope includes: an objective optical system configured to form a subject image; a movable lens configured to adjust an image forming state of the objective optical system; an actuator including a magnet configured to move integrally with the movable lens and a coil configured to cause the movable lens and the magnet to move by electromagnetic force by applying a drive signal; a position sensor configured to output a position detection signal showing a position of the movable lens according to a density of a magnetic flux generated by the magnet; and an endoscope memory storing at least one piece of correction information for correcting a crosstalk influence on the position detection signal given by a density of a magnetic flux generated by the coil to which the drive signal is applied; and the processor includes a controller configured to correct the position detection signal acquired from the position sensor, based on the drive signal and the at least one piece of correction information acquired from the endoscope memory, and output the drive signal generated by feedback control based on at least one target position of the movable lens and the position detection signal that is corrected, to the actuator.

A processor according to one aspect of the present invention is connected to an endoscope, the endoscope including: an objective optical system configured to form a subject image; a movable lens configured to adjust an image forming state of the objective optical system; an actuator including a magnet configured to move integrally with the movable lens and a coil configured to cause the movable lens and the magnet to move by electromagnetic force by applying a drive signal; a position sensor configured to output a position detection signal showing a position of the movable lens according to a density of a magnetic flux generated by the magnet; and an endoscope memory storing at least one piece of correction information for correcting a crosstalk influence on the position detection signal given by a density of a magnetic flux generated by the coil to which the drive signal is applied; and the processor including a controller configured to correct the position detection signal acquired from the position sensor based on the drive signal and the at least one piece of correction information acquired from the endoscope memory, and output the drive signal generated by feedback control based on at least one target position of the movable lens and the position detection signal that is corrected, to the actuator.

An endoscope according to one aspect of the present invention is connected to a processor, the endoscope including: an objective optical system configured to form a subject image; a movable lens configured to adjust an image forming state of the objective optical system; an actuator including a magnet configured to move integrally with the movable lens and a coil configured to cause the movable lens and the magnet to move by electromagnetic force by applying a drive signal; a position sensor configured to output a position detection signal showing a position of the movable lens according to a density of a magnetic flux generated by the magnet; and an endoscope memory storing at least one piece of correction information for correcting a crosstalk influence on the position detection signal given by a density of a magnetic flux generated by the coil to which the drive signal is applied.

BRIEF DESCRIPTION OF THE DRAWINGS

FIG. 8 is a flowchart showing details of feedback control at step S8 in FIG. 6 in the above embodiment.

DETAILED DESCRIPTION OF THE
PREFERRED EMBODIMENT

An embodiment of the present invention will be described below with reference to drawings.

Figure 1:
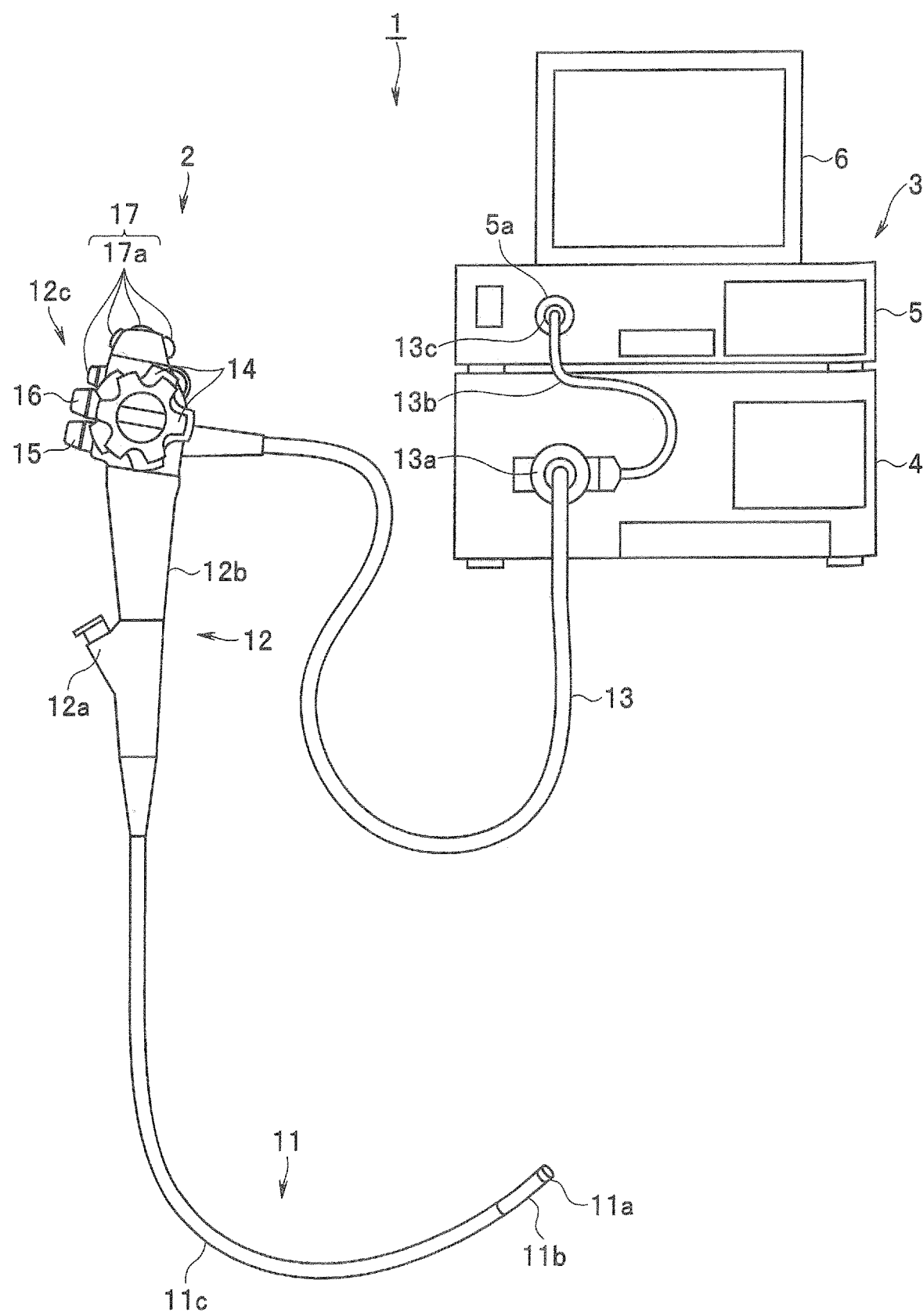
FIG. 1 is a diagram showing a configuration of an endoscope system in which an endoscope and a processor are attachably and detachably configured, in an embodiment of the present invention.

FIGS. 1 to 8 show an embodiment of the present invention, and FIG. 1 is a diagram showing a configuration of an endoscope system 1 in which an endoscope 2 and a processor 3 are attachably and detachably configured.

The endoscope system 1 as an image pickup apparatus in the present embodiment is configured, for example, as an electronic endoscope system that picks up an optical image of a subject and outputs an image pickup signal. Here, the endoscope system 1 may be any of endoscope systems for medical, industrial, academic and other purposes.

The endoscope system 1 is provided with the endoscope 2 and the processor 3 configured as a body separate from the endoscope 2. The processor 3 is provided with a light source device 4 configured to emit illumination light, a video processor 5 configured to process an image pickup signal from the endoscope 2, and a monitor 6 configured to display an endoscopic image based on a video signal outputted from the video processor 5. Note that the monitor 6 is not limited to being included in the processor 3, but a separate external monitor may be connected to the processor 3 and used. The light source device 4 may be configured integrally with the video processor 5.

The endoscope 2 is provided with an elongated insertion portion 11 to be inserted into a subject, an operation portion 12 provided on a proximal end side of the insertion portion 11, and a universal cord 13 extended, for example, from a side portion of the operation portion 12, and is configured as an electronic endoscope as described later. However, the endoscope 2 is not limited to an electronic endoscope but may be an optical endoscope if the endoscope 2 is configured to drive an objective optical system 21 (see FIGS. 2 and 3, and the like) by an actuator 23 (see FIGS. 2 and 3, and the like) described later.

The insertion portion 11 is provided with a distal end portion 11a, a bending portion 11b and a flexible tube portion 11c in that order from a distal end side toward the proximal end side. Note that though a case where the endoscope 2 is a flexible endoscope is given as an example here, the endoscope 2 may be a rigid endoscope.

Inside the distal end portion 11a, the objective optical system 21, an image pickup device 22 (see FIG. 2), the actuator 23, magnets 24 (see FIGS. 2 and 3, and the like), a position sensor 25 (see FIGS. 2 and 3, and the like) and the like are arranged.

The operation portion 12 is provided with a forceps opening 12a, a grip portion 12b and a user operation portion 12c.

The forceps opening 12a is an opening portion on a proximal end side of a forceps channel provided in the insertion portion 11. An opening portion on a distal end side of the forceps channel is arranged at the distal end portion 11a. By inserting a treatment instrument such as forceps from the forceps opening 12a and causing the treatment instrument to project from the distal end portion 11a, various kinds of treatment for a subject by the treatment instrument can be performed.

The grip portion 12b is a part that a surgeon who operates the endoscope 2 grasps by his hand.

The user operation portion 12c is a part for the surgeon to perform various kinds of operations for the endoscope system 1 including the endoscope 2.

The user operation portion 12c is provided with two bending operation portions 14, an air/water feeding button 15, a suction button 16 and a switch portion 17.

One of the two bending operation portions 14 is for performing a bending operation of the bending portion 11b in a vertical direction, and the other is for performing a bending operation of the bending portion 11b in a horizontal direction. It is possible to perform a bending operation of the bending portion 11b in a desired direction by combining vertical bending and horizontal bending.

The air/water feeding button 15 is an operation button for performing air/water feeding to the distal end portion 11a side, for example, via the forceps channel described above.

The suction button 16 is an operation button for performing suction from the distal end portion 11a side, for example, via the forceps channel described above.

The switch portion 17 is configured being provided with a plurality of switches 17a, and mainly operations related to image pickup are performed by the switch portion 17. For example, a certain switch 17a is adapted to function as a release button for picking up a still image; another certain switch 17a is adapted to function as a freeze button for freezing video that is being observed on the monitor 6; and still another certain switch 17a is adapted to function as a focus button for adjusting a focus position of the objective optical system 21 (or a zoom button for adjusting a zoom position).

The universal cord 13 includes a light guide bundle and a signal line. Here, the light guide bundle is for transmitting illumination light generated by the light source device 4 to radiate the illumination to a subject from an illumination window on the distal end portion 11a. The signal line is used for transmission of various kinds of signals related to image pickup of the image pickup device 22, various kinds of signals related to driving of the actuator 23 and position detection, and endoscope information, and the like.

A scope connector 13a to be detachably connected to the light source device 4 is provided on a proximal end of the universal cord 13. By connecting the scope connector 13a to the light source device 4, a state in which illumination light can be supplied to a proximal end of the light guide bundle is entered.

For example, from a side portion of the scope connector 13a, the scope cable 13b that includes the signal line described above is extended. An electrical connector 13c to be detachably connected to the video processor 5 is provided on a proximal end of the scope cable 13b. By connecting the electrical connector 13c to a connector receptacle 5a of the video processor 5, an electrical circuit of the endoscope 2 and an electrical circuit of the video processor 5 are connected via the signal line. Note that the scope cable 13b may be attachable to and detachable from the scope connector 13a, or the universal cord 13 and the scope cable 13b may be integrally configured.

The video processor 5 supplies power to the endoscope 2 to control an electrical configuration of the endoscope 2. The video processor 5 also processes an image pickup signal obtained from the image pickup device 22 of the endoscope 2 to generate a video signal.

The monitor 6 is configured, for example, as a color monitor and is connected to the video processor 5. The monitor 6 receives a video signal processed by the video processor 5 and displays an endoscopic image. Furthermore, the monitor 6 is adapted to be capable of displaying various kinds of information and the like related to the endoscope system 1.

Figure 2:
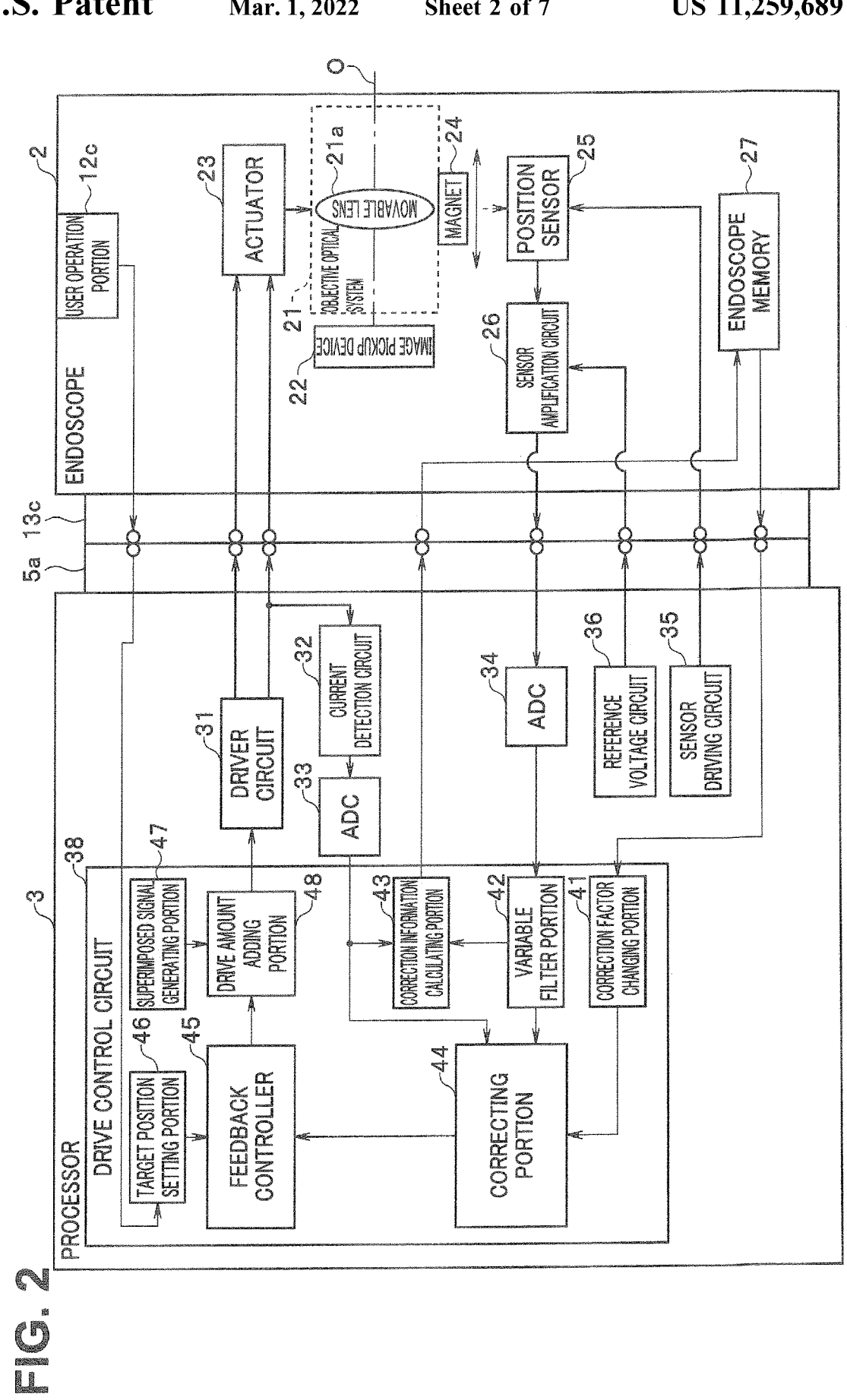
FIG. 2 is a diagram showing main parts of electrical and optical configurations of the endoscope and the processor related to driving of an objective optical system in the above embodiment.

FIG. 2 is a diagram showing main parts of electrical and optical configurations of the endoscope 2 and the processor 3 related to driving of the objective optical system 21. Note that, in FIG. 2, thin arrows show a flow of a digital signal, and normal-thickness arrows show a flow of an analog signal (however, FIG. 2 shows a mere example of classification of the digital signal and the analog signal).

The endoscope 2 is provided with the objective optical system 21, the image pickup device 22, the actuator 23, the magnets 24, the position sensor 25 and the user operation portion 12c as described above and is further provided with a sensor amplification circuit 26 and an endoscope memory 27.

The objective optical system 21 forms an optical image of a subject (a subject image) on an image pickup surface of the image pickup device 22. The objective optical system 21 is provided with a movable lens 21a and a fixed lens 21b (see FIG. 3). The movable lens 21a is for adjusting an image-forming state of the objective optical system 21. The movable lens 21a is movable in a direction of an optical axis O of the objective optical system 21, facing the fixed lens 21b. When the movable lens 21a moves in the direction of the optical axis O, the image forming state of the objective optical system 21 is adjusted, and, for example, the focus position (which may instead be the zoom position) is changed. Therefore, the movable lens 21a functions, for example, as a focus lens (or a zoom lens). Note that though the movable lens 21a is given as an example of a movable optical element here, the movable optical element is not limited to a lens, but other optical elements such as an optical filter, an optical diaphragm and a mirror are also possible.

A plurality of pixels are arrayed on an image pickup surface of the image pickup device 22, and the image pickup device 22 generates an image pickup signal configured with a plurality of pixel signals by performing photoelectric conversion of a subject image formed by the objective optical system 21 by each pixel. Note that an image pickup system of the image pickup apparatus is configured including the objective optical system 21 and the image pickup device 22.

The actuator 23 moves the movable lens 21a in the direction of the optical axis O and is specifically configured as a voice coil motor (VCM) configured to cause driving force to be generated by electromagnetic force.

The magnets 24 are configured with permanent magnets or the like and are arranged to move in the direction of the optical axis O integrally with the movable lens 21a. Magnetic fields generated by the magnets 24 are used for the position sensor 25 to detect a position of the movable lens 21a that moves integrally with the magnets 24.

Furthermore, the magnets 24 of the present embodiment are not only used for position detection but also configured to also serve as a part of the voice coil motor in order to miniaturize the distal end portion 11a. Therefore, the actuator 23 configured as the voice coil motor includes the magnets 24 and coils 23a and 23b (see FIG. 3 and the like) described later.

Figure 3:
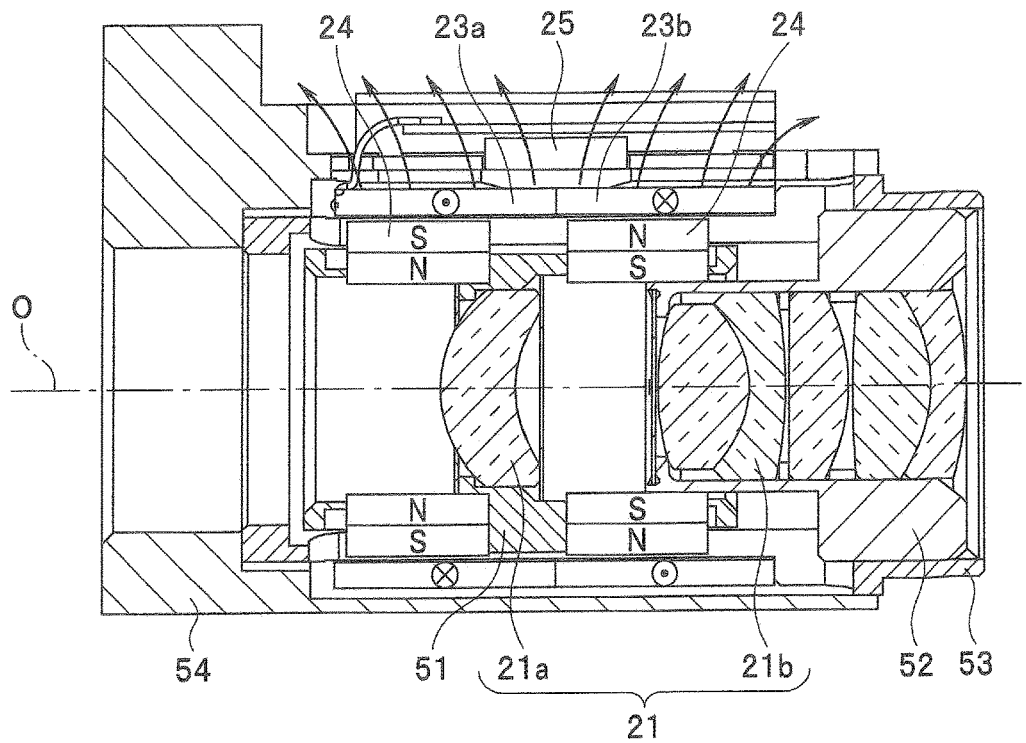
FIG. 3 is a cross-sectional view showing configurations of the objective optical system and an actuator in the above embodiment.

Here, FIG. 3 is a cross-sectional view showing configurations of the objective optical system 21 and the actuator 23. Note that, in FIG. 3, a left side indicates a distal end side (an object side) and a right side indicates a proximal end side (an image side). An observation window not shown is provided on a distal end side of the objective optical system 21.

The movable lens 21a is held, for example, by a movable barrel 51 that is movable in the direction of the optical axis O within a predetermined range. The fixed lens 21b is, for example, held by a lens barrel 52 and then fixed to a fixed barrel 53. Furthermore, the fixed barrel 53 is fixed to a distal end portion body 54 provided in the distal end portion 11a of the insertion portion 11.

The magnets 24 are fixed to the movable barrel 51, and the coils 23a and 23b of the actuator 23 are attached to a fixed portion such as the fixed barrel 53.

In the configuration example shown in FIG. 3, the magnets 24 are provided at two positions on the distal end side and the proximal end side in the direction of the optical axis O, respectively, and magnetized in a radial direction around the optical axis O. Magnetization directions of the magnet 24 on the distal end side and the magnet 24 on the proximal end side are opposite to each other. More specifically, an outer diameter side and an inner diameter side of the magnet 24 on the distal end side are an S-pole and an N-pole, respectively; and an outer diameter side and an inner diameter side of the magnet 24 on the proximal end side are an N-pole and an S-pole, respectively.

The coil 23a is provided facing the magnet 24 on the distal end side, and the coil 23b is provided facing the magnet 24 on the proximal end side. Both of the coils 23a and 23b are wound in a circumferential direction around the optical axis O. Furthermore, in response to the magnetization directions of the magnet 24 on the distal end side and the magnet 24 on the proximal end side being opposite to each other, a direction of a current applied to the coil 23a and a direction of a current applied to the coil 23b are opposite directions around the optical axis O (if one is a clockwise direction around the optical axis O, the other is a counterclockwise direction around the optical axis O).

At a middle position between the coils 23a and 23b in the direction of the optical axis O on an outer peripheral side of the coils 23a and 23b, the position sensor 25 is fixed to the distal end portion body 54. In other words, the position sensor 25 is arranged on the fixed portion side, facing the magnets 24, with the coils 23a and 23b being sandwiched between the position sensor 25 and the magnets 24.

The position sensor 25 outputs a position detection signal showing the position of the movable lens 21a according to a density of a magnetic flux generated by the magnets 24. More specifically, the position sensor 25 is configured using a magnetic sensor such as a hall element configured to output a position detection signal (a hall detection signal) according to the magnetic flux density of a magnetic field generated by the magnets 24. In other words, since the density of the magnetic flux that enters the position sensor 25 changes when the magnets 24 move facing the position sensor 25, it is possible to, by detecting a voltage (a hall voltage) of a position detection signal, know positions of the magnets 24, therefore, the position of the movable lens 21a that moves integrally with the magnets 24.

However, as seen from the arrangement in FIG. 3, the position sensor 25 is arranged close to the coils 23a and 23b in the small-size actuator 23 arranged in the distal end portion body 54 of the endoscope 2. Therefore, a density of a magnetic flux generated when a current is applied to the coils 23a and 23b (indicated by arrows in FIG. 3) is also detected by the position sensor 25.

In other words, when a current is applied to the coils 23a and 23b to move the movable lens 21a, a voltage obtained by a change in a hall voltage by the density of the magnetic flux generated from the coils 23a and 23b being added to a hall voltage by the density of the magnetic flux generated from the magnet 24 is the hall voltage detected by the position sensor 25.

Thus, a signal due to the magnetic flux from the coils 23a and 23b (appropriately referred to as a leakage magnetic flux) is superimposed on a position detection signal outputted from the position sensor 25, in addition to an original signal showing the position of the movable lens 21a. The signal due to the leakage magnetic flux becomes a noise signal (a false signal) at the time of detecting the position of the movable lens 21a.

The noise signal due to the leakage magnetic flux not only causes position detection accuracy to decrease but also influences stability at the time of performing feedback control. Therefore, correction information for correcting the noise signal is determined and stored in the endoscope memory 27 as described later. In the feedback control, influence of the leakage magnetic flux (a false signal component) included in the position detection signal is corrected using the correction information read from the endoscope memory 27.

Here, the magnitude of the noise signal (the false signal) due to the leakage magnetic flux differs according to each individual endoscope 2 because of mechanical variation, electrical variation and assembly variation among endoscopes 2. Therefore, for each individual endoscope 2, a correction coefficient K (see Formula 1 and the like described later) that gives a relationship between a current for a drive signal applied to the coils 23a and 23b and a position detection signal outputted from the position sensor 25 when the current is applied is acquired as the correction information.

In the configuration as described above, the movable lens 21a, the movable barrel 51 and the magnets 24 constitute a movable portion, and other portions constitute a fixed portion. The fixed portion is fixed to the distal end portion 11a and holds the movable portion such that the movable portion can move in the direction of the optical axis O within a predetermined range.

By applying a current to the coils 23a and 23b that are in a magnetic field generated by the magnets 24, a Lorentz force occurs in the coils 23a and 23b, and the movable portion moves in the direction of the optical axis O due to reaction of the Lorentz force because the fixed barrel 53 is fixed.

Note that a reason why the moving magnet type voice coil motor is adopted here is that it is possible to more easily miniaturize the actuator 23 by the configuration of applying a current to the fixed portion side than by a configuration of applying a current to the movable portion side (because it is necessary to use, for example, a flexible printed circuit board and the like to apply a current to the movable portion side the position of which moves). Therefore, adoption of a moving coil type voice coil motor is not prohibited.

The sensor amplification circuit 26 shown in FIG. 2 is configured as a differential amplification circuit configured to amplify a hall voltage of an analog position detection signal outputted from the position sensor 25.

The endoscope memory 27 is a nonvolatile memory storing correction information for correcting an error that occurs in a position detection signal for each individual endoscope 2.

More specifically, the endoscope memory 27 stores such correction information for correcting crosstalk influence on a position detection signal given by the density of the magnetic flux generated by the coils 23a and 23b to which a drive signal has been applied as described above. Here, a shift of a position detection signal due to the crosstalk influence (a noise signal component) not only differs according to models of endoscopes 2 but also differs for each individual endoscope 2 even among endoscopes 2 of the same model. Therefore, as described later, the correction information is measured for each individual endoscope 2 and stored in the endoscope memory 27.

Further, the endoscope memory 27 stores a correction factor $\alpha$ with a value larger than 0 and equal to or smaller than 1, which is preferably determined according to characteristics of the actuator 23 (therefore, the correction factor $\alpha$ differs for each of models of endoscopes 2, and, furthermore, may differ for each production lot if the mounted actuator 23 is changed according to the manufacture lot of endoscope 2).

In addition, the endoscope memory 27 further stores model information (such as a model number) and a serial number of the endoscope 2, other various kinds of information related to the endoscope 2, and the like.

As described above, the user operation portion 12c is provided with the switches 17a for adjusting the image forming state (the focus position, the zoom position and the like) of the objective optical system 21 as described above. In other words, by a user operating the user operation portion 12c, an instruction signal showing a target position of the movable lens 21a is transmitted from the user operation portion 12c to the processor 3 side. As an example, it is set which of a far-point focus position (a normal position) and a near-point focus position (a near position) is to be selected as the target position of the movable lens 21a by the user operation portion 12c (however, the setting is not limited to two-point focusing of far-point and near-point focusing, and it is, of course, possible to continuously change the focus position (or the zoom position)).

Note that though manual focusing by setting from the user operation portion 12c has been described here, focusing is not limited to the manual focusing, but auto-focusing or the like based on an image pickup signal obtained from the image pickup device 22 may be performed.

As described above, the endoscope 2 is attachable to and detachable from the processor 3 by detachably connecting the scope connector 13a to the light source device 4 and detachably connecting the electrical connector 13c to the connector receptacle 5a of the video processor 5.

A signal transmitted/received between the endoscope 2 and the processor 3 via the electrical connector 13c and the connector receptacle 5a is, for example, as follows.

The endoscope 2 transmits an instruction signal from the user operation portion 12c, a position detection signal from the sensor amplification circuit 26 and data such as the correction information in the endoscope memory 27 to the processor 3. Further, the endoscope 2 receives a drive signal to the actuator 23, power supply and a reference voltage signal to the sensor amplification circuit 26, and a hall element current signal to the position sensor 25, from the processor 3. Furthermore, the endoscope 2 is adapted to, when a predetermined operation condition, a calibration mode as a specific example, is set, receive correction information calculated by the processor 3 and store the correction information into the endoscope memory 27.

The processor 3 controls the endoscope system 1 to emit illumination light by the light source device 4 and acquires an image pickup signal from the endoscope 2. The video processor 5 processes the image pickup signal to generate a video signal, outputs the video signal to the monitor 6 to causes an endoscopic image and the like to be displayed on the monitor 6. Since publicly known techniques can be appropriately used for the above configuration and operation related to the processor 3, detailed description will be omitted.

As components related to driving of the objective optical system 21, the processor 3 is provided with a driver circuit 31, a current detection circuit 32, an ADC 33, an ADC 34, a sensor driving circuit 35, a reference voltage circuit 36 and a drive control circuit 38.

The driver circuit 31 outputs a drive signal to the actuator 23 to drive the actuator 23, based on control by the drive control circuit 38. More specifically, by the driver circuit 31 applying a drive signal with a predetermined current value to the coils 23a and 23b, the movable portion including the movable lens 21a and the magnets 24 is moved by electromagnetic force.

The current detection circuit 32 detects the current value of the drive signal supplied from the driver circuit 31 to the actuator 23 and outputs an analog current detection signal.

The ADC 33 is an analog/digital converter (an A/D converter) configured to convert an analog current detection signal outputted from the current detection circuit 32 to a digital current detection signal.

The ADC 34 is an analog/digital converter (an A/D converter) configured to convert an analog position detection signal acquired from the position sensor 25 and amplified by the sensor amplification circuit 26 to a digital position detection signal.

The sensor driving circuit 35 is a constant current circuit configured to supply a hall element current, which is a constant current, to the position sensor 25 configured, for example, as a hall element.

The reference voltage circuit 36 supplies an offset voltage signal to be a reference voltage, to the sensor amplification circuit 26 configured, for example, as a differential amplification circuit.

The drive control circuit 38 is configured, for example, including an arithmetic processing circuit such as a CPU and a memory, and is adapted to fulfill a function as each processing portion. Here, in the memory of the drive control circuit 38, model information (such as a model number) and a serial number of the processor 3, a processing program executed by the processor 3, various kinds of parameters used in the processor 3, set values set for the endoscope system 1 by the user, other various kinds of information related to the processor 3 and the like are stored.

The drive control circuit 38 is a controller configured to control the driver circuit 31 so that the position of the movable lens 21a shown by a position detection signal corresponds to a target position shown by an instruction signal from the user operation portion 12c.

More specifically, the drive control circuit 38 includes a correction factor changing portion 41, a variable filter portion 42, a correction information calculating portion 43, a correcting portion 44, a feedback controller 45, a target position setting portion 46, a superimposed signal generating portion 47 and a drive amount adding portion 48.

The correction factor changing portion 41 reads the correction information and the correction factor α from the endoscope memory 27 and adaptively changes the correction factor α acquired from the endoscope memory 27 so that the value is smaller in the case of prioritizing stability of feedback control than in the case of prioritizing accuracy of a position detection signal. Then, the correction factor changing portion 41 outputs the correction information read from the endoscope memory 27 and the correction factor α that has been adaptively changed, to the correcting portion 44. Note that if the correction factor α is not adaptively changed, the correction factor changing portion 41 may be omitted.

The variable filter portion 42 performs filter processing (low-pass filter processing) of causing a signal component with a frequency equal to or below a cutoff frequency to pass through and reducing a signal component with a frequency higher than the cutoff frequency, for a position detection signal acquired from the position sensor 25, and outputs the position detection signal to the correcting portion 44. The variable filter portion 42 is configured to be capable of causing the cutoff frequency to change at this time.

The variable filter portion 42 sets a first cutoff frequency lower than a frequency of a superimposed signal when the predetermined operation condition (the calibration mode or the like) is not set, and sets a second cutoff frequency higher than the frequency of the superimposed signal if the predetermined operation condition is set.

When the predetermined operation condition (the calibration mode or the like) is set, the correction information calculating portion 43 calculates correction information.

More specifically, if the predetermined operation condition is set, the correction information calculating portion 43 acquires a position detection signal from the position sensor 25 via the variable filter portion 42 and acquires a current detection signal showing a current value of a drive signal (including a superimposed signal) to be applied to the actuator 23, from the ADC 33. Furthermore, the correction information calculating portion 43 extracts a current value component of the superimposed signal in the current detection signal and detects an amplitude of a signal component synchronized with the superimposed signal, in the position detection signal. Then, the correction information calculating portion 43 calculates a ratio of the amplitude of the signal component synchronized with the superimposed signal, in the position detection signal to an amplitude of the current value component of the superimposed signal (more specifically, the correction factor K described later) as the correction information.

When the predetermined operation condition (the calibration mode or the like) is set, the correction information calculated by the correction information calculating portion 43 is stored into the endoscope memory 27.

Based on the drive signal (more specifically, the current value of the drive signal acquired from the ADC 33) to the actuator 23 and the correction information acquired from the endoscope memory 27, the correcting portion 44 corrects a noise signal component due to the density of the magnetic flux generated from the coils 23a and 23b, in the position detection signal acquired from the position sensor 25. More specifically, the correcting portion 44 corrects the position detection signal by subtracting a signal obtained by multiplying the drive signal by the correction information (the correction coefficient K described later) from the position detection signal.

Note that if the correction factor changing portion 41 described above is provided, the correcting portion 44 further corrects the correction information (the correction factor K described later) acquired from the endoscope memory 27 using the correction factor α changed by the correction factor changing portion 41, and corrects the position detection signal acquired from the position sensor 25 based on the corrected correction information and the drive signal.

The feedback controller 45 outputs a drive signal generated by feedback control based on the target position of the movable lens 21a and the position detection signal corrected by the correcting portion 44, to the actuator 23, and the feedback controller 45 constitutes a part of the controller.

More specifically, the feedback controller 45 generates a control signal for causing the driver circuit 31 to output a drive signal with such a constant current value that a difference between a current position of the movable lens 21a shown by the position detection signal outputted from the correcting portion 44 and the target position of the movable lens 21a shown by an instruction signal from the user operation portion 12c becomes 0.

Further, when the predetermined operation condition (the calibration mode or the like) is set, the feedback controller 45 generates a drive signal for performing servo control so that the target position is a certain position (the target position is kept at a certain position).

The target position setting portion 46 sets the target position of the movable lens 21a based on the instruction signal from the user operation portion 12c.

When the predetermined operation condition (the calibration mode or the like) is set, the superimposed signal generating portion 47 generates and outputs a superimposed signal which is an alternating current signal (for example, a sine-wave alternating current signal) with an amplitude and a frequency for a shift amount of the position of the movable lens 21a to be a shift amount that the feedback controller 45 regards as a stoppage.

Figure 4:
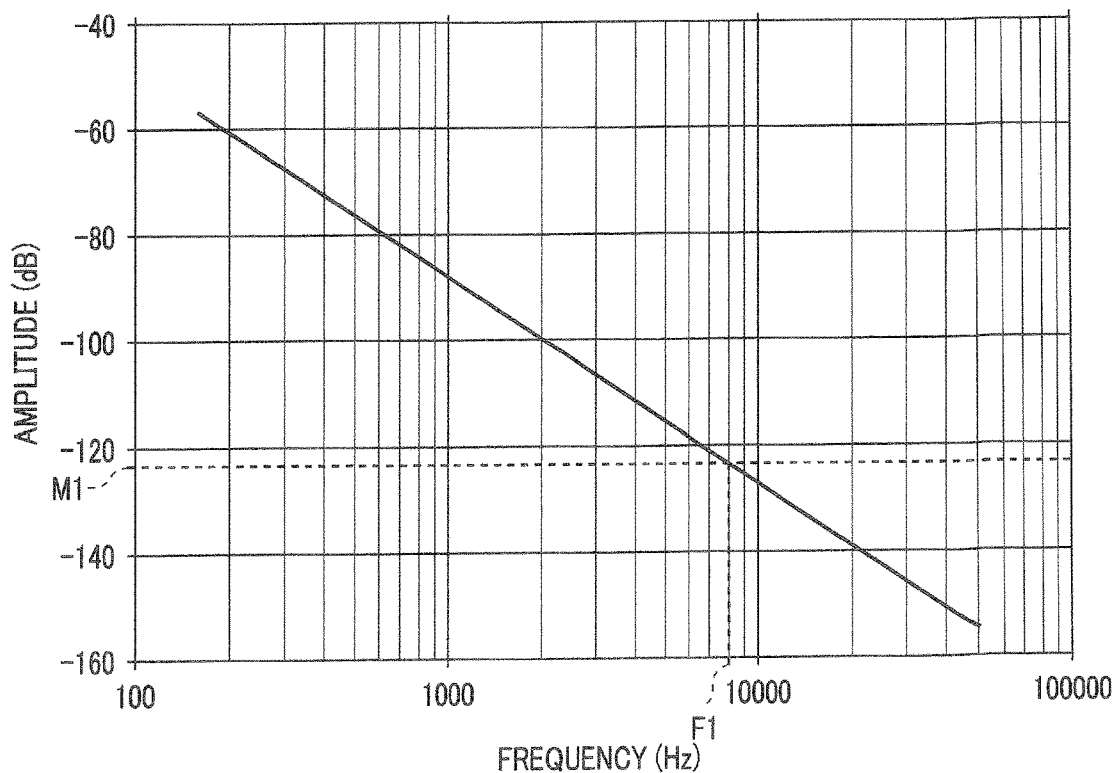
FIG. 4 is a chart showing a relationship between a frequency of an alternating current drive signal applied to the actuator and an amplitude that occurs on a driven movable portion in the above embodiment.

Here, FIG. 4 is a chart showing a relationship between a frequency of an alternating current drive signal applied to the actuator 23 and an amplitude that occurs on the movable portion that has been driven. FIG. 4 shows a state of the amplitude that occurs on the movable portion when an alternating current with a constant amplitude is applied to the actuator 23 while the frequency is changed.

The voice coil motor has a characteristic of being difficult to move when a frequency of an applied current becomes high. More specifically, when an alternating current with a constant amplitude is applied to the actuator 23, and a frequency of the applied alternating current is increased, an amplitude of an oscillation that occurs on the movable portion gradually decreases as shown in FIG. 4. (Note that since the amplitude of the oscillation that occurs on the movable portion increases if the amplitude of the alternating current is increased in a state of the frequency being fixed, FIG. 4 shows frequency characteristics when the amplitude is constant.)

The shift amount that the feedback controller 45 regards as a stoppage is, for example, a shift amount corresponding to a signal value below accuracy of bit conversion by the ADC 34 (corresponding to an upper limit threshold M1 of the amplitude in FIG. 4). In other words, when an amplitude of a position detection signal outputted by the position sensor 25 and amplified by the sensor amplification circuit 26 becomes below the bit conversion accuracy of A/D conversion by the ADC 34, the feedback controller 45 regards the movable lens 21a as being stopped from a viewpoint of measurement accuracy.

Thus, the superimposed signal generating portion 47 generates a superimposed signal with a certain amplitude and a frequency higher than F1 so that the amplitude of the oscillation that occurs on the movable portion becomes the shift amount that the feedback controller 45 regards as a stoppage (a shift amount smaller than the upper limit threshold M1). Here, F1 is a frequency threshold corresponding to the upper limit threshold M1.

Note that the shift amount that the feedback controller 45 regards as a stoppage is not limited to the above. For example, even in the case of a shift amount equal to or above the accuracy of bit conversion by the ADC 34, the bit value of which fluctuates, the shift amount may be treated as the shift amount regarded as a stoppage if the bit value fluctuation is within a certain range, and the feedback controller 45 regards the bit value fluctuation as an error.

The drive amount adding portion 48 superimposes the superimposed signal outputted from the superimposed signal generating portion 47 on a drive signal outputted from the feedback controller 45 and outputs the drive signal on which the superimposed signal is superimposed, to the actuator 23 via the driver circuit 31, and the drive amount adding portion 48 constitutes a part of the controller.

Figure 5:
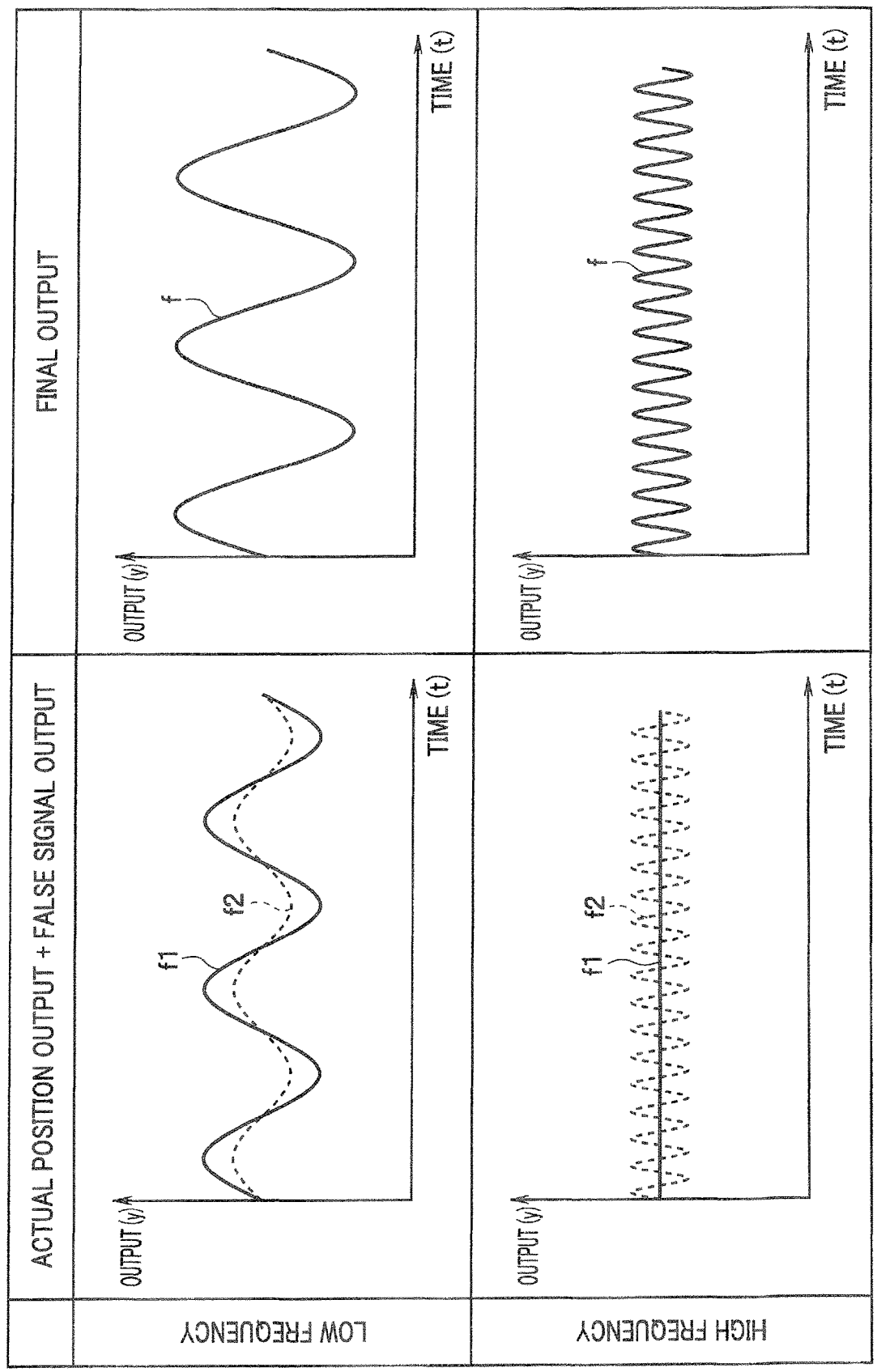
FIG. 5 shows charts showing examples of a position detection signal when the drive signal has a low frequency and a position detection signal when the drive signal has a high frequency in the above embodiment.

FIG. 5 shows charts showing examples of a position detection signal when a drive signal has a low frequency and a position detection signal when the drive signal has a high frequency.

Low frequency fields in FIG. 5 show a state in which, when an alternating current signal with a frequency lower than the frequency threshold F1 described above is applied to the actuator 23, a noise signal (a false signal) f2 due to the leakage magnetic flux from the coils 23a and 23b is superimposed on an actual position detection signal f1 indicating the position of the movable lens 21a. (A left field shows f1 and f2 separately, and a right field shows a position detection signal f obtained by superimposing f2 on f1.)

High frequency fields in FIG. 5 show a state in which, when a superimposed signal, which is an alternating current signal with a frequency higher than the frequency threshold F1 (for example, a frequency of about 10 K(Hz) in the characteristic diagram in FIG. 4) is superimposed on a drive signal for servo-controlling the movable lens 21a to a certain target position, and the drive signal on which the superimposed signal is superimposed is applied to the actuator 23, a noise signal (a false signal) f2 due to the leakage magnetic flux from the coils 23a and 23b is superimposed on an actual position detection signal f1 indicating the position of the movable lens 21a. (A left field shows f1 and f2 separately, and a right field shows a position detection signal f obtained by superimposing f2 on f1.) As seen from FIG. 5, the actual position detection signal f1 indicates that the movable lens 21a is at the certain target position, that is, a signal value indicating movement of the movable lens 21a does not fluctuate. Therefore, an amplitude of the position detection signal f becomes an amplitude of the noise signal (the false signal) f2, and it is possible to easily extract only the amplitude of the noise signal (the false signal) f2.

Note that a method is also conceivable in which, without providing the superimposed signal generating portion 47 or the drive amount adding portion 48, the target position is caused to change by a sine wave with a frequency higher than the frequency threshold F1 by the target position setting portion 46. In this case, however, since such control is performed that the target position of the movable lens 21a forms a sine wave, a drive signal outputted from the driver circuit 31 does not necessarily become an accurate sine wave, and the measurement accuracy may decrease. Therefore, by providing the superimposed signal generating portion 47 and the drive amount adding portion 48 so that the drive signal outputted from the driver circuit 31 becomes an accurate sine wave, the measurement accuracy is improved.

Figure 6:
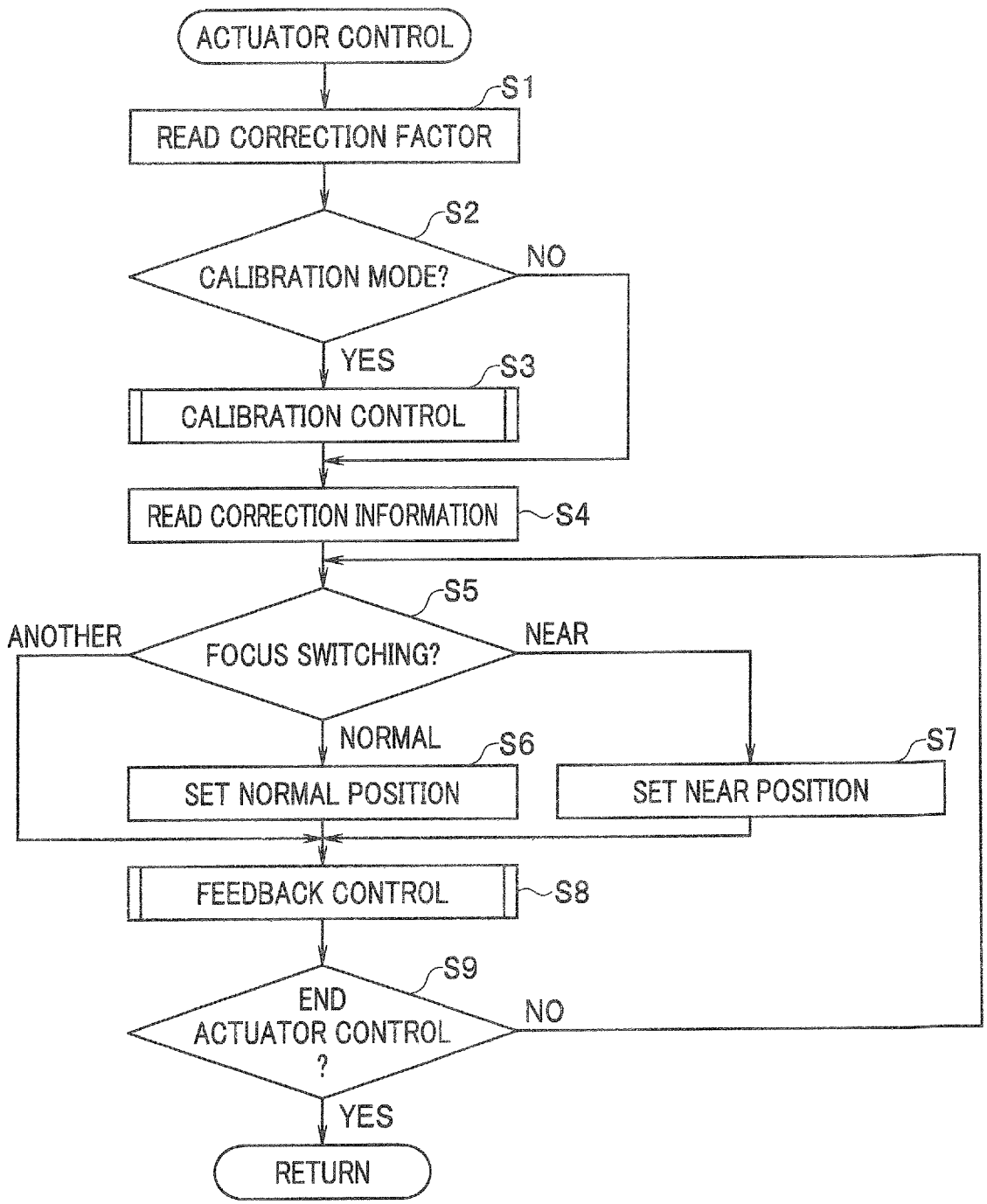
FIG. 6 is a flowchart showing an actuator control process in the endoscope system of the above embodiment.

FIG. 6 is a flowchart showing an actuator control process in the endoscope system 1.

When the processor 3 connected to the endoscope 2 is powered on or when the endoscope 2 is connected to the processor 3 that is powered on, the actuator control process is executed from a main process not shown, the main process being executed by the processor 3 after various kinds of initialization is performed.

When the process starts, the drive control circuit 38 acquires the correction factor α from the endoscope memory 27 first (step S1) and judges whether or not to enter the calibration mode (step S2).

Here, it is judged to enter the calibration mode if correction information has not been recorded in the endoscope memory 27 yet, and it is judged not to enter the calibration mode if correction information has already been recorded. However, whether or not to enter the calibration mode is not limited to the above. Even if the correction information has been already recorded in the endoscope memory 27, the calibration mode may be set at the time of maintenance or the like.

If it is judged at step S2 that the calibration mode is to be entered, calibration control is performed (step S3).

Figure 7:
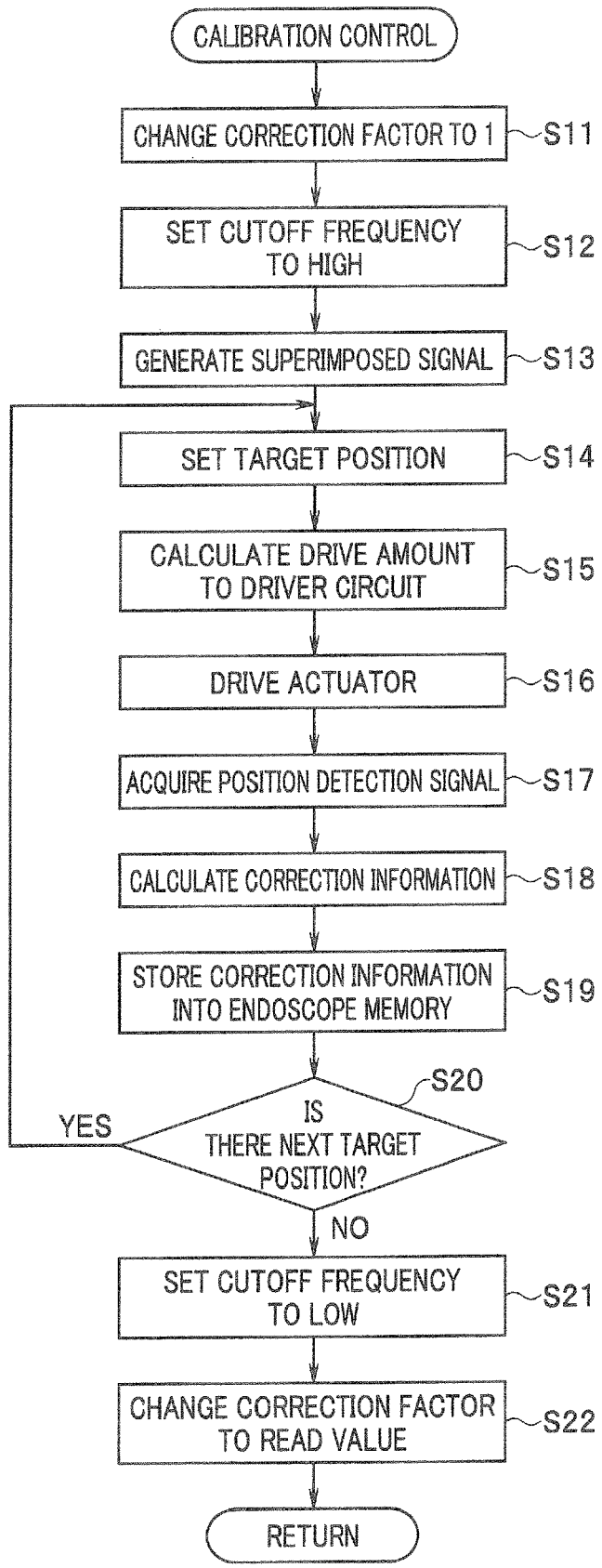
FIG. 7 is a flowchart showing details of calibration control at step S3 in FIG. 6 in the above embodiment.

Here, FIG. 7 is a flowchart showing details of the calibration control at step S3 in FIG. 6.

When the process is entered, the correction factor changing portion 41 changes the correction factor α to 1 (that is, 100%) irrespective of a value of the correction factor α acquired at step S1 (step S11).

Furthermore, the variable filter portion 42 sets the cutoff frequency to the second cutoff frequency that is higher than a frequency of an alternating current superimposed signal generated by the superimposed signal generating portion 47 (step S12). Here, since the frequency of the superimposed signal is higher than the frequency threshold F1 as described above, the second cutoff frequency is naturally higher than the frequency threshold F1.

Note that if noise with a frequency higher than the frequency of the superimposed signal does not influence the position detection accuracy, the low-pass filter processing by the variable filter portion 42 may be turned off (all-pass characteristics may be set) instead of setting the second cutoff frequency.

Then, the superimposed signal generating portion 47 generates and outputs a superimposed signal (step S13). Note that, for the frequency and amplitude of the superimposed signal, particular values applicable to any of endoscopes 2 of respective models, or the frequency and amplitude may be adaptively set according to the kind of the actuator 23 mounted on the endoscope 2.

After that, the feedback controller 45 sets a target position of the movable lens 21*a* (step S14).

Here, it is more general to think that a magnitude of a noise signal due to the leakage magnetic flux that is included in a position detection signal differs according to the position of the movable lens 21*a*.

Therefore, it is preferred to not only measure a magnitude of a noise signal when the movable lens 21*a* is at one particular position but also measure magnitudes of noise signals when the movable lens 21*a* is at a plurality of different particular positions. This is because it becomes possible thereby to determine a magnitude of a noise signal when the movable lens 21*a* is at an arbitrary position by interpolation calculation or the like.

Therefore, the feedback controller 45 is adapted to set one or more (preferably a plurality of) target positions of the movable lens 21*a* in the calibration mode. For example, in the case of performing the two-point focusing as described above, each of the far-point focus position (the normal position) and the near-point focus position (the near position) may be set as a target position.

Note that, in order to avoid the movable portion from hitting an end part of the movement range, each target position is set to be away from the end part of the movement range of the movable portion by a predetermined distance or more. Consequently, it is possible to prevent breakage and the like of the actuator 23.

Furthermore, the feedback controller 45 performs servo control and calculates a drive amount of the driver circuit 31 so that the movable lens 21*a* is maintained at a target position (step S15).

The drive amount adding portion 48 superimposes the superimposed signal from the superimposed signal generating portion 47 on a drive signal from the feedback controller 45 and outputs the drive signal on which the superimposed signal is superimposed, to the driver circuit 31, and the driver circuit 31 drives the actuator 23 (step S16).

After that, the correction information calculating portion 43 acquires a position detection signal from the position sensor 25 via the variable filter portion 42 (step S17) and calculates correction information based on the acquired position detection signal and the current value of the drive signal acquired from the current detection circuit 32 via the ADC 33 (step S18).

More specifically, when an amplitude (an amplitude of a current value) of the superimposed signal on the drive signal applied to the actuator 23 from the driver circuit 31 is indicated by Iamp, and an amplitude of a signal component synchronized with the superimposed signal, in the position detection signal acquired from the variable filter portion 42 is indicated by B amp, the correction factor K as the correction information is calculated by Formula 1 below:

$$K = Bamp/Iamp \qquad \text{[Formula 1]}$$

Here, since the position detection signal that the correction information calculating portion 43 acquires from the position sensor 25 is a signal that has passed through a position detection signal transmission route such as the sensor amplification circuit 26, the calculated correction factor K is such that responds to variation in characteristics of individual position detection signal transmission routes.

The correction information calculating portion 43 causes the correction factor K thus calculated to be stored into the endoscope memory 27 as correction information (step S19).

Note that since the correction information is information depending on each individual endoscope 2, the process of calculating correction information and storing the correction information into the endoscope memory 27 is preferably performed at the time of inspection at factory shipment of the endoscope 2.

After that, the feedback controller 45 judges whether there is a next target position or not (step S20). If judging that the next target position exists, the feedback controller 45 returns to step S14 described above and sets the next target position of the movable lens 21*a*.

In this way, the feedback controller 45 preferably sets a plurality of target positions to be servo-controlled; the correction information calculating portion 43 calculates a plurality of pieces of correction information for the set plurality of target positions, respectively; and the endoscope memory 27 stores the plurality of pieces of correction information in association with the plurality of target positions, respectively.

If the process is performed for all the target positions, it is judged at step S20 that there is not a next target position.

At this time, the variable filter portion 42 sets the cutoff frequency to the first cutoff frequency that is lower than the frequency of the alternating current superimposed signal generated by the superimposed signal generating portion 47 (step S21). Consequently, removal of high-frequency noise from the position detection signal outputted from the ADC 34 is performed as usual.

Furthermore, after the correction factor changing portion 41 returns the correction factor α set to 1 at step S11 to the value acquired from the endoscope memory 27 at step S1 (step S22), the flow returns to the process of FIG. 6.

Thus, if the calibration control at step S3 ends, or it is judged at step S2 not to enter the calibration mode, the correcting portion 44 acquires the correction information (more specifically, the correction factor K described above) from the endoscope memory 27 via the correction factor changing portion 41 (step S4).

Then, according to whether there is an instruction signal from the user operation portion 12c or not and according to content of the instruction signal, it is judged whether or not a focus switching operation has been performed on the user operation portion 12c. If the focus switching operation has been performed, it is further judged whether an instructed target position is the near-point focus position (the near position) or the far-point focus position (the normal position) (step S5). If the focus switching operation has not been performed, it is judged that the target position is another position.

Here, if it is judged that the operation of focus switching to the normal position has been performed, the target position setting portion 46 sets the target position to the normal position (step S6).

If it is judged at step S5 that the operation of focus switching to the near position has been performed, the target position setting portion 46 sets the target position to the near position (step S7).

If it is judged at step S5 that the target position is another position, the current target position is maintained as it is.

Then, feedback control for causing the movable lens 21a to be close to the set target position is performed (step S8).

Here, FIG. 8 is a flowchart showing details of the feedback control at step S8 in FIG. 6.

When the process is entered, the correcting portion 44 acquires the position detection signal from the variable filter portion 42 (step S31) and corrects the position detection signal (step S32).

Here, when the position detection signal acquired from the variable filter portion 42 is indicated by P, and a current value of the drive signal acquired from the ADC 33 is indicated by I, the correcting portion 44 corrects the position detection signal P to calculate a corrected position detection signal P' by specifically performing calculation as shown by Formula 2 below.

$$P' = P - \alpha \times K \times I \quad \text{[Formula 2]}$$

On a right side of Formula 2, K×I indicates a noise signal (false signal) component included in the position detection signal P when the drive signal with the current value I is applied to the coils 23a and 23b of the actuator 23.

At the time of performing normal-time feedback control for causing the movable lens 21a to move to a target position, control stability is prioritized, and a result of multiplying the noise signal (false signal) component (K×I) by the correction factor α equal to or smaller than 1 (preferably smaller than 1) is subtracted from the position detection signal P. Note that since the current value I may be positive or negative according to whether the movable portion is moved to the object side or to the image side, a second term on the right side of Formula 2 may reduce or increase a value of a first term on the right side.

Here, in the case of performing the two-point focusing, if each of a correction factor corresponding to the near-point focus position (the near position) and a correction factor corresponding to the far-point focus position (the normal position) is stored in the endoscope memory 27 as the correction factor K, the necessity to perform interpolation calculation is eliminated, and a processing load is reduced. It is preferably possible to perform accurate correction.

In the case of performing multipoint focusing (or multipoint zooming) with three or more points or focusing to continuous positions (or zooming to continuous focal lengths), interpolation calculation or the like is performed from a plurality of correction factors K to determine a correction factor corresponding to a target position as necessary, and the correction factor is used for correction.

The position detection signal V corrected in this way is outputted from the correcting portion 44 to the feedback controller 45.

The feedback controller 45 calculates such a drive signal that a position shown by the position detection signal P' corresponds to the target position set by the target position setting portion 46 (step S33).

The drive signal calculated in this way is outputted from the feedback controller 45 to the driver circuit 31 via the drive amount adding portion 48. During normal operation other than the calibration mode, since the superimposed signal generating portion 47 does not generate a superimposed signal, the driver circuit 31 applies a drive signal from the feedback controller 45 to the actuator 23 to drive the actuator 23 (step S34).

When the process of step S34 is performed, the flow returns to the process shown in FIG. 6.

When the feedback control at step S8 is performed in this way, it is judged whether or not to end the actuator control (step S9).

If it is judged not to end the actuator control, the flow returns to step S5 described above, and feedback control according to focus switching is performed. The control from steps S5 to S9 is repeatedly performed for each predetermined sampling time period.

On the other hand, if it is judged to end the actuator control at step S9, the flow returns to the main process not shown.

According to the embodiment as described above, since a position detection signal is corrected based on a drive signal to the actuator 23 for driving the movable lens 21a and correction information acquired from the endoscope memory 27, a position of the movable lens 21a can be more accurately acquired. As a result, it becomes possible to more accurately feedback-control the movable lens 21a to move to a target position.

Further, when the calibration mode or the like is set, a superimposed signal for obtaining a shift amount regarded as a stoppage is generated, superimposed on a drive signal for causing the movable lens 21a to be at a certain target position and outputted to the actuator 23; and a ratio of an amplitude of a signal component synchronized with the superimposed signal, in the position detection signal to an amplitude of the superimposed signal is calculated as correction information and stored in the endoscope memory 27. Therefore, a device or a mechanism for locking the movable portion is not required, and the correction information for correcting the position detection signal can be acquired in a state in which the movable portion is incorporated in the objective optical system 21.

Furthermore, since the shift amount that the feedback controller 45 regards as a stoppage is a shift amount corresponding to a signal value below the accuracy of bit conversion by the ADC 34 configured to perform A/D conversion of the position detection signal, it is possible to regard the shift amount as a stoppage from a viewpoint of detection accuracy, without requiring a particular configuration or the like for controlling the shift amount regarded as a stoppage.

Since, by subtracting a signal obtained by multiplying a drive signal by the correction information acquired from the endoscope memory 27, from a position detection signal acquired from the position sensor 25, the position detection signal is corrected, it is possible to perform calculation with a low load at a high speed, and it is possible to improve real-time processing.

In addition, if a plurality of target positions are set, a plurality of pieces of correction information are calculated, and the plurality of pieces of correction information are stored in the endoscope memory 27 in association with the plurality of target positions, respectively, it becomes possible to obtain correction information for an arbitrary target position by interpolation calculation or the like.

Further, if the calibration mode or the like is not set, a first cutoff frequency lower than a frequency of a superimposed signal is set. Therefore, it is possible to suppress high-frequency noise and acquire a highly accurate position detection signal.

On the other hand, if the calibration mode or the like is set, a second cutoff frequency higher than a frequency of a superimposed signal is set. Therefore, a noise signal (false signal) component based on the superimposed signal does not attenuate, and it is possible to appropriately acquire correction information.

Furthermore, the correction factor α is adaptively changed so that the value is smaller in the case of prioritizing stability of feedback control than in the case of prioritizing the accuracy of a position detection signal. Therefore, it is possible to provide the endoscope system 1 in which both of highly accurate position detection and drive stability are enabled.

More specifically, since the correction factor α is set to 1 during correction information calculation in which the position detection accuracy is important, it is possible to highly accurately calculate correction information.

Further, since the correction factor α is set to a value determined according to the characteristics of the actuator 23 during normal feedback control in which drive stability of the actuator 23 is important, it is possible to perform stable driving.

Note that the process of each portion described above may be performed by one or more processors configured as hardware. For example, each portion may be a processor configured as an electronic circuit, or may be a circuit portion in a processor configured with an integrated circuit such as an FPGA (field programmable gate array). Alternatively, a processor configured with one or more CPUs may execute a function as each portion by reading and executing the processing program recorded in a recording medium.

Though description has been made above mainly on an endoscope system, an operation method for causing an endoscope system to operate as described above, a processing program for causing a computer to perform processes similar to processes of an endoscope system, a computer-readable non-transitory recording medium in which the processing program is recorded, and the like are also possible.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope system comprising an endoscope and a processor to which the endoscope is connected, wherein
the endoscope comprises:
an objective optical system configured to form a subject image;
a movable lens configured to adjust an image forming state of the objective optical system;
an actuator comprising a magnet configured to move integrally with the movable lens and a coil configured to cause the movable lens and the magnet to move by electromagnetic force by applying a drive signal;
a position sensor configured to output a position detection signal showing a position of the movable lens according to a density of a magnetic flux generated by the magnet; and
an endoscope memory storing at least one piece of correction information for correcting a crosstalk influence on the position detection signal given by a density of a magnetic flux generated by the coil to which the drive signal is applied;
the processor comprises a controller configured to correct the position detection signal acquired from the position sensor, based on the drive signal and the at least one piece of correction information acquired from the endoscope memory, and output the drive signal generated by feedback control based on at least one target position of the movable lens and the position detection signal that is corrected, to the actuator;
when a predetermined operation condition is set, the controller generates a superimposed signal which is an alternating current signal with an amplitude and a frequency for a shift amount of the position of the movable lens to be a shift amount that the controller regards as a stoppage, generates the drive signal for performing servo control so that the at least one target position becomes a certain position, superimposes the superimposed signal on the generated drive signal to output the drive signal on which the superimposed signal is superimposed, to the actuator, detects an amplitude of a signal component synchronized with the superimposed signal, in the position detection signal acquired from the position sensor, and calculates a ratio of the amplitude of the signal component to the amplitude of the superimposed signal as the at least one piece of correction information; and
the endoscope memory stores the at least one piece of correction information that is calculated.

2. The endoscope system according to claim 1, wherein
the processor further comprises an A/D converter configured to convert the position detection signal acquired from the position sensor, which is analog, to the position detection signal which is digital; and
the shift amount that the controller regards as a stoppage is a shift amount corresponding to a signal value below accuracy of bit conversion by the A/D converter.

3. The endoscope system according to claim 1 wherein the controller corrects the position detection signal acquired from the position sensor by subtracting a signal obtained by multiplying the drive signal by the at least one piece of correction information acquired from the endoscope memory, from the position detection signal.

4. The endoscope system according to claim 1, wherein
the controller sets a plurality of the target positions that are servo-controlled, and calculates a plurality of the pieces of correction information for the set plurality of the target positions, respectively; and
the endoscope memory stores the plurality of the pieces of correction information in association with the plurality of the target positions, respectively.

5. The endoscope system according to claim 1, wherein
the controller is configured to correct the position detection signal acquired from the position sensor after performing filter processing for causing a signal component with a frequency equal to or lower than a cutoff frequency to pass through and reducing a signal component with a frequency higher than the cutoff frequency, for the position detection signal and configured to be capable of causing the cutoff frequency to change; and
the controller sets a first cutoff frequency lower than the frequency of the superimposed signal if the predetermined operation condition is not set, and sets a second cutoff frequency higher than the frequency of the superimposed signal if the predetermined operation condition is set.

6. The endoscope system according to claim 1, wherein
the endoscope memory further stores a correction factor with a value larger than 0 and equal to or lower than 1, the correction factor being determined according to characteristics of the actuator;
the controller adaptively changes the correction factor acquired from the endoscope memory so that the value is smaller in a case of prioritizing stability of the feedback control than in a case of prioritizing accuracy of the position detection signal, corrects the at least one piece of correction information acquired from the endoscope memory using the changed correction factor, and corrects the position detection signal acquired from the position sensor based on the at least one piece of correction information that is corrected and the drive signal.

7. A processor connected to an endoscope, the endoscope comprising:
an objective optical system configured to form a subject image;
a movable lens configured to adjust an image forming state of the objective optical system;
an actuator comprising a magnet configured to move integrally with the movable lens and a coil configured to cause the movable lens and the magnet to move by electromagnetic force by applying a drive signal;
a position sensor configured to output a position detection signal showing a position of the movable lens according to a density of a magnetic flux generated by the magnet; and
an endoscope memory storing at least one piece of correction information for correcting a crosstalk influence on the position detection signal given by a density of a magnetic flux generated by the coil to which the drive signal is applied; and
the processor comprising a controller configured to correct the position detection signal acquired from the position sensor based on the drive signal and the at least one piece of correction information acquired from the endoscope memory, and output the drive signal generated by feedback control based on at least one target position of the movable lens and the position detection signal that is corrected, to the actuator;
wherein when a predetermined operation condition is set, the controller generates a superimposed signal which is an alternating current signal with an amplitude and a frequency for a shift amount of the position of the movable lens to be a shift amount that the controller regards as a stoppage, generates the drive signal for performing servo control so that the at least one target position becomes a certain position, superimposes the superimposed signal on the generated drive signal to output the drive signal on which the superimposed signal is superimposed, to the actuator, detects an amplitude of a signal component synchronized with the superimposed signal, in the position detection signal acquired from the position sensor, calculates a ratio of the amplitude of the signal component to the amplitude of the superimposed signal as the at least one piece of correction information, and causes the endoscope memory to store the at least one piece of correction information that is calculated.

8. The processor according to claim 7, further comprising an A/D converter configured to convert the position detection signal acquired from the position sensor, which is analog, to the position detection signal which is digital;
wherein the shift amount that the controller regards as a stoppage is a shift amount corresponding to a signal value below accuracy of bit conversion by the A/D converter.

9. The processor according to claim 7, wherein the controller corrects the position detection signal acquired from the position sensor by subtracting a signal obtained by multiplying the drive signal by the at least one piece of correction information acquired from the endoscope memory, from the position detection signal.

10. The processor according to claim 7, wherein the controller sets a plurality of the target positions that are servo-controlled, and calculates a plurality of the pieces of correction information for the set plurality of the target positions, respectively, and causes the endoscope memory to store the plurality of the pieces of correction information in association with the plurality of the target positions, respectively.

11. The processor according to claim 7, wherein
the controller is configured to correct the position detection signal acquired from the position sensor after performing filter processing for causing a signal component with a frequency equal to or lower than a cutoff frequency to pass through and reducing a signal component with a frequency higher than the cutoff frequency, for the position detection signal and configured to be capable of causing the cutoff frequency to change; and
the controller sets a first cutoff frequency lower than the frequency of the superimposed signal if the predetermined operation condition is not set, and sets a second cutoff frequency higher than the frequency of the superimposed signal if the predetermined operation condition is set.

12. The endoscope system according to claim 7, wherein the controller acquires a correction factor with a value larger than 0 and equal to or lower than 1 from the endoscope memory, the correction factor being determined according to characteristics of the actuator, adaptively changes the correction factor so that the value is smaller in a case of prioritizing stability of the feedback control than in a case of prioritizing accuracy of the position detection signal, corrects the at least one piece of correction information acquired from the endoscope memory using the changed correction factor, and corrects the position detection signal acquired from the position sensor based on the at least one piece of correction information that is corrected and the drive signal.

* * * * *